United States Patent [19]

Wathen et al.

[11] Patent Number: 4,784,771
[45] Date of Patent: Nov. 15, 1988

[54] METHOD AND APPARATUS FOR PURIFYING FLUIDS

[75] Inventors: Ronald L. Wathen; Steven L. Miller, both of Jefferson County, Ky.

[73] Assignee: Environmental Water Technology, Inc., Ky.

[21] Appl. No.: 80,968

[22] Filed: Aug. 3, 1987

[51] Int. Cl.⁴ .............................................. B01D 13/00
[52] U.S. Cl. ..................................... 210/636; 210/639; 210/655; 210/96.2; 210/126; 210/195.2; 210/257.2
[58] Field of Search ................ 210/636, 639, 652–655, 210/96.2, 126, 128, 129, 195.2, 257.2

[56] References Cited

U.S. PATENT DOCUMENTS

| | | | |
|---|---|---|---|
| 3,616,921 | 11/1971 | Bray | 210/257.2 X |
| 3,654,148 | 4/1972 | Bradley | 210/636 |
| 3,756,408 | 9/1973 | Spatz et al. | 210/96.2 X |
| 3,956,114 | 5/1976 | Del Pico et al. | 210/636 |
| 3,992,301 | 11/1976 | Shippey et al. | 210/636 |
| 4,069,155 | 1/1978 | Tsujimoto et al. | 210/257.2 X |
| 4,166,031 | 8/1979 | Hardy | 210/636 X |
| 4,293,409 | 10/1981 | Riede et al. | 210/96.2 |
| 4,342,651 | 8/1982 | Ahrens | 210/195.2 X |
| 4,361,485 | 11/1982 | Boonstra | 210/636 |
| 4,508,622 | 4/1985 | Polaschegg et al. | 210/96.2 |
| 4,528,093 | 7/1985 | Winer | 210/96.2 |
| 4,574,049 | 3/1986 | Pittner | 210/639 |
| 4,623,467 | 11/1986 | Hamlin | 210/652 |
| 4,629,568 | 12/1986 | Ellis, III | 210/636 |
| 4,695,385 | 9/1987 | Boag | 210/636 |

Primary Examiner—Robert Spitzer
Attorney, Agent, or Firm—Ralph B. Brick

[57] ABSTRACT

A method and apparatus for purifying and/or separating fluids including passing such fluid from a feed side of a reverse osmosis unit to the product side of such unit and to an ultimate user during a purifying cycle and recirculating residual fluid back to the feed side in by-pass relation to the reverse osmosis unit during a treating cycle to introduce suitable treating fluids into the system for disinfecting and rejuvenating the system.

39 Claims, 4 Drawing Sheets

METHOD AND APPARATUS FOR PURIFYING FLUIDS

BACKGROUND OF THE INVENTION

The present invention relates to a method and apparatus for purifying and separating fluids and more particularly to a unique and novel method and apparatus for purifying fluids such as water for purposes requiring high purification characteristics, including but not limited to medical endeavors such as is required in kidney dialysis and as is often required in fluid-dependent equipment and procedures in scientific laboratories wherein fluid purification and/or separation is required.

A number of arrangements to purify and/or separate fluids, such as water, have been utilized in the past which have employed the well known principle of reverse osmosis. In accordance with the general principle of osmosis, fluid is passed through a membrane boundary separating two solutions of differing solvent activity. The direction of solvent flow across the membrane boundary under an osmotic gradient or pressure difference is always from the more dilute into the more concentrated solution. In reverse osmosis, solvent flows across the membrane boundary from the more concentrated to the less concentrated solution when pressure application exceeds the osmotic pressure difference. The rate of flow at which reverse osmosis occurs is a direct function of the membrane constant, membrane area and pressure employed and is usually an inverse function of membrane thickness.

The past arrangements which have employed reverse osmosis have, for the most part, been complex and expensive in manufacture, assembly and maintenance, and have presented frequent user problems often resulting in undesirable and possibly dangerous risks to the ultimate user or to the end equipment involved. In the prior art among the numerous fluid processing arrangements known to employ the principle of reverse osmosis for fluid purification purposes, three such known arrangements have employed recirculation of purified fluid received in storage containers from the product side of the reverse osmosis unit back to the feed side of the unit, with one such arrangement even employing an osmotically active chemical treating substance in a back-flush sequence to kill organisms. In this regard, attention is directed to U.S. Pat. No. 3,616,921, issued to Donald T. Bray on Nov. 2, 1971 and U.S. Pat. No. 3,654,148, issued to William E. Bradley on Apr. 4, 1972, wherein, to extend continuous utilization of the purification system, means is employed to pass relatively pure fluid from one or more storage containers either in the form of helical elongated pipes or tanks communicating with the product side of a reverse osmosis unit back to the feed side of the reverse osmosis unit for further purification, U.S. Pat. No. 3,654,148 further including utilization of osmotically active chemicals to obtain osmotic back flushing of the membrane. Attention is further directed to U.S. Pat. No. 4,629,568, issued to George S. Ellis, III, wherein pressure sensing sequences are utilized to cause fluid to flow from storage containers communicating with the product side of a reverse osmosis unit back to the input or feed side. Although these more recent reverse osmosis arrangements have broadly recognized the desirability of fluid recirculation, they have required utilization of elaborate, complex and time-consuming storage containers and conduit recirculating arrangements without concern for or recognition of possible user misoperation and undesirable contaminant build-up on both feed and product sides of a reverse osmosis unit.

The present invention provides a highly efficient and economical reverse osmosis arrangement which recirculates treated fluid from the product side of a reverse osmosis unit directly without storage to the feed side with a minimum of steps and parts and with a minimum of consumer shutdown time, reducing manufacturing, assembly and operation costs and at the same time minimizing user steps, storage requirements and risks of accident to the ultimate consumer. In addition, the present invention provides a reverse osmosis arrangement which facilitates ready adaptation to modular implementation and computer control. As will be seen more fully hereinafter, the present invention permits further ready disinfection and rejuvenation including rinsing of the purifying apparatus and fluid treatment containers assuring a thorough treatment of the reverse osmosis unit, including a shear-like effect by providing a path of fluid flow transverse the path of fluid flow through the membrane of the reverse osmosis unit, without the possible damaging reverse flushing and pulsing requirements of the past and without time-consuming and comparatively complex storage arrangements and, at the same time, with minimum risks to equipment and to ultimate user during treating or cleansing and flushing or rinsing stages. In addition, the present invention provides a unique and novel fluid purification and/or separation arrangement which not only assures full, thorough and efficient disinfection and rejuvenation, including rinsing/flushing of the purifying equipment to permit effective removal of both chemical and microbial contaminants on both feed and product sides thereof, but which minimizes disinfecting and rejuvenating carry-over risks during on-line fluid purifying and/or separation operations. Further the present invention provides a novel disinfection/rejuvenation arrangement, the arrangement including but not limited to disinfection/rejuvenation and flushing treatments being accomplished efficiently and positively through quick connect and flow control mechanisms coupled to the fluid purifying apparatus permitting simple, straightforward, efficient and safer user operations.

Various other features of the present invention will become obvious to one skilled in the art upon reading the disclosure set forth herein.

SUMMARY OF THE INVENTION

More particularly the present invention provides a fluid purification and fluid separation apparatus comprising: a primary flow conduit having spaced upstream fluid feed inlet means and downstream fluid product outlet means; a reverse osmosis means disposed in the primary flow conduit between the fluid feed inlet means and the fluid product outlet means to include a feed side and a product side; motive means communicating with the primary flow conduit to enhance fluid flow from the feed inlet means through the reverse osmosis means to the product outlet means; treatment means connectable into the primary flow conduit to selectively introduce a separate treating fluid into the primary flow conduit to treat the reverse osmosis means; and, a secondary flow global loop conduit connectable to extend parallel the primary flow conduit in by-pass relation to the reverse osmosis means to communicate directly between the product outlet means and the feed inlet means of the primary conduit and with the treatment means to treat the reverse osmosis means when a separate treating fluid is selectively introduced into the treatment means. Further, the present invention provides a unique method of purifying a fluid utilizing a reverse osmosis process comprising the steps of: passing fluid to be purified during a purifying cycle through an open ended feed zone, through a reverse osmosis zone to an open ended inlet product zone and to an end user for a preselected time period; interrupting the purifying cycle after the preselected time period by closing the feed and product zones and recycling residual fluid in by-pass relation to the reverse osmosis zone from the product zone to the feed zone for a preselected time period during a treating cycle; and, introducing treating fluid into the recycled fluid during the treating cycle to rejuvenate the reverse osmosis unit for preselected time periods during the treating cycle. Among a number of other features of the present invention, a novel arrangement is prvvided which serves to drain fluid in the system in the event such fluid in the primary flow conduit reaches a sensed level not user suitable, including a novel arrangement for interrupting the sensing arrangement during treating periods. Further, a novel arrangement is provided which permits system rejuvenation including the treatment containers. It is to be understood that various changes can be made by one skilled in the art in one or more of the several parts of the apparatus disclosed or in one or more of the several steps of the method disclosed without departing from the scope or spirit of the present invention.

BRIEF DESCRIPTION OF THE DRAWINGS

Referring to the drawings which schematically disclose one advantageous embodiment of the present invention:

Referring to FIG. 1, which schematically discloses the several parts of the inventive apparatus, the inventive fluid purification arrangement is broadly referred to by reference numeral 2. This arrangement includes a primary flow conduit 3 having a spaced upstream fluid feed inlet 4 and a downstream fluid product outlet 6. A main "on-off" supply valve 7, which can be manually operated or operated through a suitable solenoid control as part of operating circuitry (not shown), can be positioned in primary conduit 3 immediately adjacent fluid feed inlet 4. Positioned in primary conduit 3 downstream of and adjacent supply valve 7 is a rinse or flushing control mechanism 8 which includes "on-off" flushing valve 9 and parallel flow control restrictor valve 11. Like valve 7 and like other valves described hereinafter, valves 9 and 11 can be manually operated or solenoid operated as part of suitable operating circuitry (not shown). The flow control restrictor 11 serves to maintain a preselected low fluid flow rate regardless of pressure in primary flow conduit 3. Such a restrictor is commercially available from sources such as the Eaton Corporation, Cleveland, Ohio. It is to be understood that instead of the flow control restrictor 11 described, it also would be possible to utilize a suitable downstream regulator in parallel with flushing valve 9, such a regulator being coordinated with the pump, hereinafter described, to maintain a preselected pump inlet flow and pressure in the primary flow conduit 3. It further is to be understood that, if desired, a suitable carbon tank 12 can be connected into the primary flow conduit 3 advantageously upstream of flushing control mechanism 8 to enhance purification of the fluid introduced into fluid inlet 4. Tank 12, which can be any one of several tanks known in the art, such as those offered by the Parks Company of St. Paul, Minn., can be connected into primary flow conduit 3 through suitable quick connect fittings 13 and 15, like those offered by the Hanson Company, Cleveland, Ohio.

Figure 1:
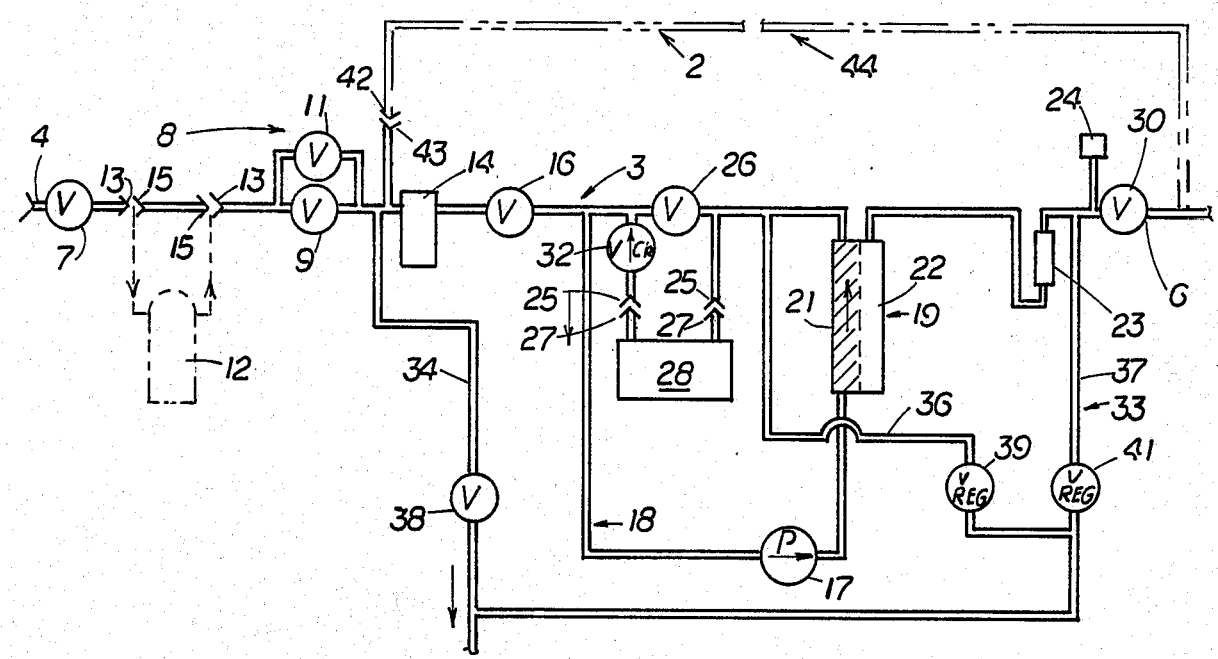
FIG. 1 is a detailed schematic view of the several parts of the apparatus employed in carrying out the present invention with a global loop not connected for treatment but shown in phantom.

Positioned downstream of flushing control mechanism 8 in conduit 3 is a suitable prefilter 14. This prefilter advantageously can be of a preselected polypropylene material sized in accordance with system demands. Such a prefilter is commercially available from the Hytrex Division, Osmonics Corp., Minnetonka, Minn. It is to be noted that a solenoid operated valve 16 is provided in the flow conduit 3, valve 16, operative by circuitry (not shown), assures fluid shut-off when shutdown of pump 17 is desired. Pump 17, which can be of a positive displacement, rotary vane type capable of operating over a broad range of high pressures and advantageously within the high pressure range of 175–200 psi also should have the ability to be coordinated with the flow control restrictor 11 (aforedescribed) to maintain a negative pump inlet below $-1$ psi during a treatment period.

The pump 17, in accordance with the present invention, is included as part of an inside conduit loop 18 which parallels primary flow conduit 3 in by-pass relation to a portion of the feed end thereof to further include the feed side 21 of a suitable reverse osmosis (RO) unit 19 downstream of pump 17. The product side 22 of reverse osmosis (RO) unit 19 connects to the product end of primary flow conduit 3 leading to a suitable flow meter 23 which serves to measure product fluid production rate. Also in primary flow circuit 3 downstream of flow meter 23 is a fluid quality monitor 24 which serves to sense and monitor the electrical conductivity/resistivity of the product fluid for reasons described hereinafter. Positioned downstream of monitor 24 is a solenoid valve 30 which valve is normally open and under closing control of monitor 24. Should monitor 24 cause closure of valve 30, excessive hydraulic back pressuring of the system is avoided by opening of pressure regulating valve 41 to drain.

Figure 2:
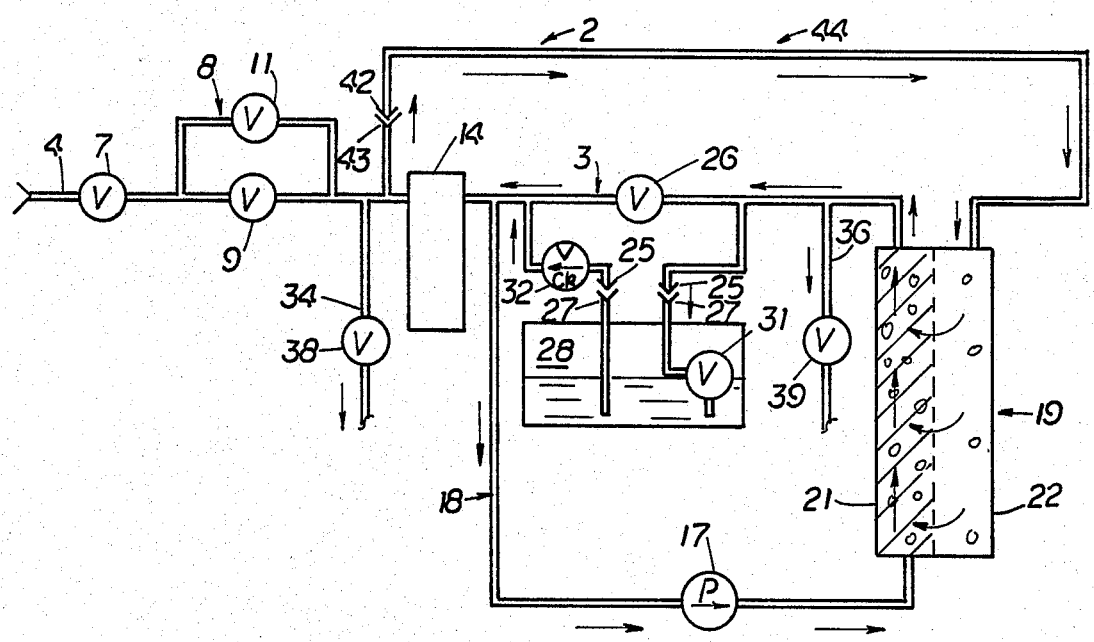
FIG. 2, for purposes of clarity, is an abbreviated schematic view of the apparatus of FIG. 1 disclosing fluid flow with the global loop connected at commencement of rejuvenating operations when an osmotically active treating fluid is employed.
Figure 3:
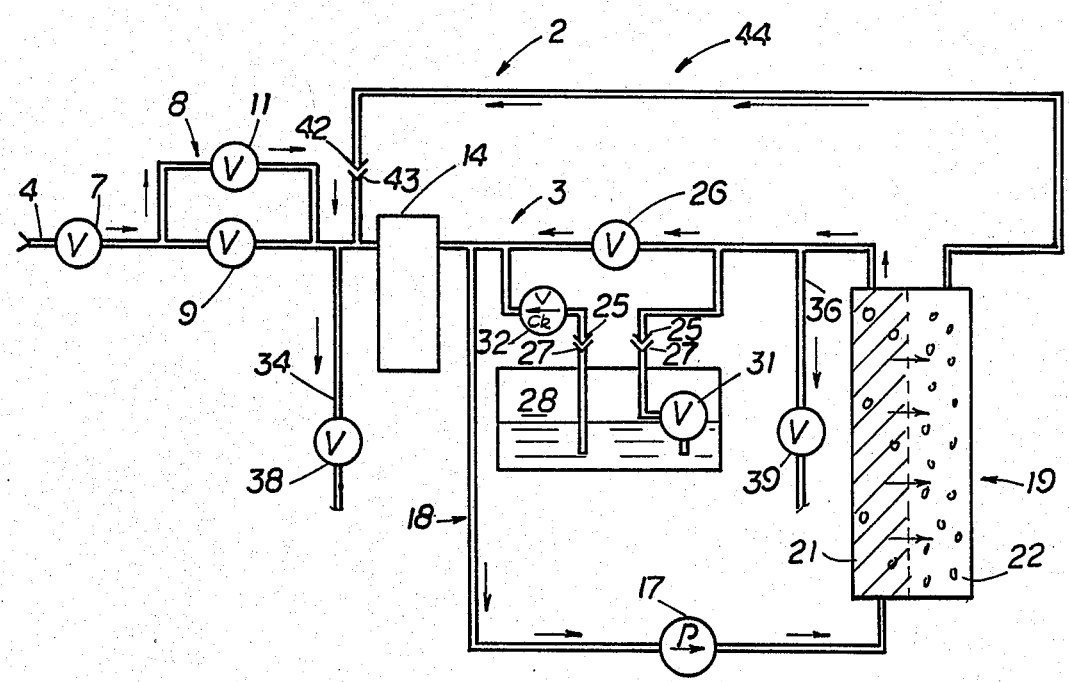
FIG. 3, for purposes of clarity, is an abbreviated schematic view similar to that of FIG. 2 with the inlet valve initially open and the global loop connected disclosing fluid flow at commencement of flushing as part of the rejuvenating operations with an osmotically active treating fluid.
Figure 4:
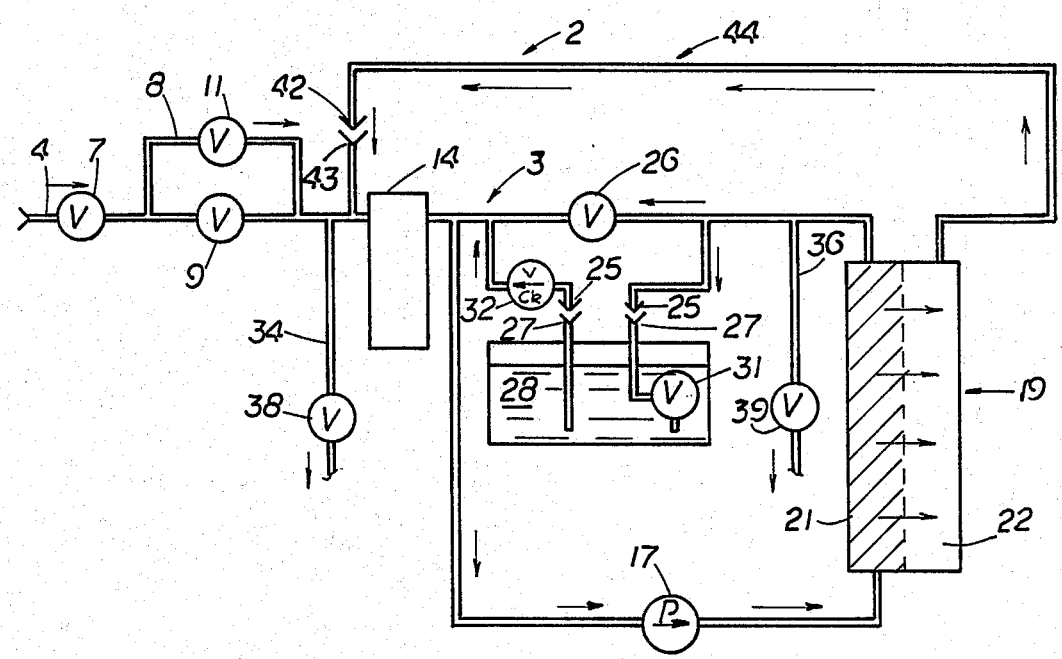
FIG. 4, for purposes of clarity, is an abbreviated schematic view similar to that of FIG. 3, with the global loop connected disclosing fluid flow near the end of flushing treatment operations when an osmotically active treating fluid is utilized.

In accordance with the present invention, included in that portion of primary flow conduit 3 which is bypassed by inside conduit loop 18 are two spaced quick connect fittings 25, similar to the quick connect fittings 13, 15 aforedescribed. These spaced quick connect fittings 25 straddle a recirculating valve 26, which can be manually or automatically operated and which during purification and treating operations is normally held in at least the partially open position. At a constant fluid production rate this valve arrangement ensures recovery, i.e., fluid product flow over fluid feed flow and, when appropriately adjusted, can serve to optimize recovery. The spaced quick connect fittings 25 serve to receive the appropriately sized and spaced quick connect fittings 27 of a vented treatment jug or container 28 for appropriate global loop treatment. The treatment jug 28 can be made from any one of a number of suitable materials and can be of a suitable plastic such as polyethylene. As can be seen in FIGS. 2-4, the jug includes an inlet level sensing and control valve 31 and an outlet which cooperates with check valve 32. It is to be understood that the capacity of jug or container 28 can be appropriately sized relative to the capacity of the overall system and it is also to be understood that additional jugs or containers can be made available for standby operations or supplementary fluid treatments. The valve 31—or some other suitable level sensing and control mechanism—can be any one of a number of commercially suitable valves such as those offered by the Fill-Pro Co. of Toronto, Canada, and advantageously is designed to provide an average forward hydraulic pressure on the feed side of the membrane regardless of the effective osmotic activity of fluid within the feed side of the system and can be set to operate in a range of slightly less than fully opened when at a low treatment fluid level position to an almost fully closed position when at a high fluid treatment level position to enhance treating operations, including disinfecting/rejuvenating and flushing and accepting both osmotically active and inactive rejuvenant fluids as will be described hereinafter. The check valve 32 can be preset to open for fluid flow at approximately 1 psi. Thus, the entire mechanism serves to minimize user risks by avoiding jug overflow and by preventing unintentional toxic fluid introduction into the system.

Again referring to FIG. 1, it is to be noted that primary flow conduit 3 is provided with a parallel drain conduit system 33, one branch 34 being connected to the feed side of conduit 3 upstream of prefilter 14, another branch 36 being connected to that feed side portion of conduit 3 within inside loop conduit 18 and a third branch 37 being connected to the primary conduit 3 on the product side of the conduit between the flow meter 23 and conductivity monitor 24. Each drain branch 34, 36, 37, is respectively provided with a suitable valve 38, 39, and 41. Valve 38 in drain branch 34 connected to primary conduit 3 before prefilter 14 serves as a straightforward manually or solenoid operated drain valve. Valve 39 in drain branch 36 connected to the feed side of the primary flow conduit 3 immediately after flow issuing from the feed side of reverse osmosis unit 19 serves as a feed water regulator and can be responsive to open to drain at a preselected line pressure. In the instant embodiment of the present invention, since pump 17 is capable of operating within a high pressure range of 175–200 psi as above discussed, valve 39 can be set to operate to open to drain at 200 psi. Valve 41 in branch 37 connected to the product side of primary conduit 3 naturally can be set to open to drain at a much lower pressure and, in the instant embodiment can be set to open to drain at 40 psi. It is to be noted that drain valve 41 can be arranged to be activated to open to drain in accordance with closure of solenoid valve 30 activated at a preselected reading on monitor 24 caused by a possible undesirable condition where the process fluid conductivity/resistivity exceeds a preset limit. When this occurs, the fluid automatically goes into a 'by-pass' mode and the process fluid passes to drain, avoiding contaminated fluid, including that which might be introduced during a treatment stage, from being delivered to its selected ultimate use, be it a kidney dialysis machine, scientific equipment or any one of a number of other end user purposes in which the inventive arrangement might be employed.

In accordance with one of the many features of the present invention to selectively deliver product fluid to the end user, primary flow conduit 3 is provided on its product side downstream of monitor 24 with quick connect fittings 42 which can be similar to quick connect fittings 13, 15, 25 and 27 above described. Quick connect fittings 42 advantageously can be mechanically or electrically linked with monitor 24 to deactivate its control over valve 30, the conductivity/resistivity sensing capability of monitor 24 remaining intact. The product side of primary flow conduit 3 carrying quick connect fittings 42 is of sufficient length to permit the quick connect fittings 42 to be coupled to quick connect branch conduit fittings 43 extending in a branch from the feed side of primary fluid conduit 3 upstream of prefilter 14. This overall loop of primary fluid conduit 3 from the product side thereof downstream of monitor 24 back to the feed side thereof at a point before prefilter 14 is referred to as global loop 44 and allows the processing fluid to be utilized in disinfecting/rejuvenating and flushing the system in a straightforward, efficient, and economical manner heretofore unknown in the fluid purification and/or separation art.

Referring to the detailed schematic and diagrammatic view of FIG. 1, fluid to be purified such as water for end use with a kidney dialysis machine is introduced at inlet 4 to the feed side of primary flow conduit 3, valves 7, 9 and 16 in primary flow conduit 3 being in the opened position and recirculating valve 26 of loop 18 in the open position. With pump 17 in the on position, the fluid to be purified is caused to pass along the feed side of primary flow conduit 3 through carbon tank 12 when connected into the primary flow conduit 3 by quick connect fittings 13 and 15, then through prefilter 14 through a portion of inside loop 18 and through reverse osmosis unit 19 to the product side of the primary conduit 3 as a purified fluid to be passed to an end use, such as a kidney dialysis machine. This purifying cycle can be varied in length and is generally commensurate with its use. In the event the electrical conductivity/resistivity of the fluid should exceed the preset limit of monitor 24 during the fluid purification cycle of operations because of improper purification conditions which may occur during the purification process, product line solenoid valve 30 closes to interrupt product water flow to user end point thereby causing valve 41 to open, passing the contaminated fluid to drain. It is to be noted that, during fluid purification operations, recirculating valve 26 in inside or nested loop 18 is maintained in a preselected partially open position to allow recirculation of fluid to be purified on the feed side of primary fluid conduit 3, placing the feed side of reverse osmosis unit 19 in a fluid reuse state, reducing supply consumption while maintaining a constant production of product fluid at a high shear-like rate to enhance purification. Further, it is to be noted that the presence of recirculation valve 26 also serves to enhance treating operation cycles by virtue of the fact that it offers some resistance to flow even when fully open.

When either or both fluid monitor 24 and/or fluid flow monitor 23 so indicate in the course of a fluid purification cycle or when an operator decides appropriately, a system treating cycle can be readily effected. Referring to the abbreviated schematic view of FIG. 2 and the legend of FIG. 5 of the drawings which disclose commencement of rejuvenating operations with an osmotically active treating fluid being positioned for introduction through connection of jug 28 containing such fluid at a preselected low level, a treatment procedure is disclosed utilizing the aforedescribed global loop 44 arrangement. To accomplish the treatment procedure, pump 17 is turned off. Valves 7, 9 and 38 are manually closed. Valve 39 is closed because of low feed pressure. Valves 11 and 32 are opened. Valve 26 is partially open and valve 31 is almost fully open. Quick connect fittings 42 is then uncoupled from user quick connect fittings (not shown) at the product side of conduit 3 and looped in global fashion to form global loop 44 around reverse osmosis unit 19 in by-pass relation therewith by readily connecting quick connect fittings 42 in coupled mating arrangement with its quick connect counterpart fittings 43 upstream of prefilter 14 on the feed side of conduit 3 with residual fluid statically remaining in global loop 44. The residual fluid serves to prevent an air build-up in the global loop. It is to be noted that when fittings 42 of primary flow conduit 3 are connected in global loop fashion to the feed side of conduit 3, the monitor 24 control over valve 30 on the product side of conduit 3 is deactivated to prevent bypass of global loop fluid contents to drain. With global loop 44 connected, jug or container 28 holding a preselected low level of a suitable treatment fluid is then coupled into nested loop 18 by mating quick connect fittings 27 with their quick connect counterpart fittings 25 which straddle recirculating valve 26 - which is advantageously maintained in partially open position as above discussed. Assuming that the treatment fluid is an osmotically active disinfecting fluid (as indicated by the bubble marks in RO unit 19 of FIG. 2), such as a solution of highly concentrated formaldehyde which can have a rejection range of approximately 38% to approximately 50% with respect to the reverse osmosis unit 19 and assuming that residual fluid remains statically in connected global loop 44 with valves 11, 32 open, valve 31 of jug 28 almost fully open and recirculating valve 26 partially open, fluid is then circulated as can be seen in FIG. 2, through reactivated pump 17, through the feed side of reverse osmosis unit 19, through partially open recirculating valve 26 and the almost fully open float valve 31 of jug 28 to entrain treatment solution through check valve 32 in closed loop 18 to enter global loop 44 through prefilter 14 in reverse order to normal fluid purification flow and around global loop 44 to the product side of reverse osmosis unit 19. Since the product side contains an osmotically active treating fluid, such as formaldehyde, the diluted static fluid on the static product side of reverse osmosis unit 19 passes in a reverse fashion through the reverse osmosis unit membrane for a period of approximately one (1) to two (2) minutes until reverse flow through the global loop 44 ceases and an equilibrium state is reached, the pump 17 being allowed to remain operational for an additional ten (10) minutes to ensure fluid distribution. The global loop 44 system is then allowed to remain in equilibrium with pump 17 turned off for approximately one and one-half (1½) to two (2) hours with the formaldehyde disinfecting the RO unit 19, prefilter 14, along with the remainder of the hydraulic system. Upon completion of the disinfection cycle, pump 17 is again activated and valve 7 is open and rinse valve 9 closed to initiate flushing (see FIGS. 3 and 5) with a restricted amount of fluid at reduced pressure passing through prefilter 14 and through loop 18, pump inlet 17, through RO unit 19, through recirculating valve 26 and jug 28 and back to inlet of pump 17. As jug 28 fills with a limited, controlled amount of flushing fluid passing through flow control restrictor 11, sensing and control valve 31 rises in the jug and the back pressure results in drain valve 39 opening to balance flushing fluid flow through the system. As the system flushes, including jug 28, concentration in the nested loop 18 reduces to produce an osmotic gradient in RO unit 19 which couples with hydraulic pressure gradient in RO unit 19 to cause fluid to pass to the product side and around global loop 18, through prefilter 14. This flushing operation from beginning to end can advantageously take approximately forty-five minutes with the above described formaldehyde disinfection, assuring flushing of the entire system including jug 28.

Figure 5:
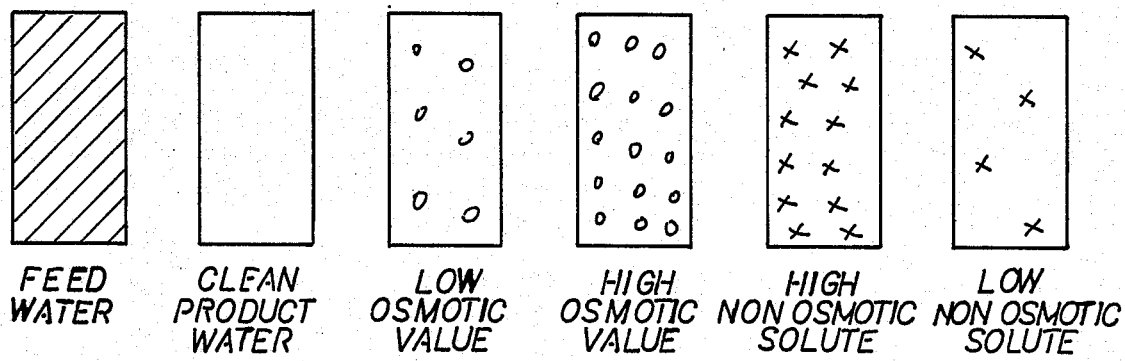

In FIGS. 4 and 5 which serve to disclose fluid flow near the end of flushing operations with the valves in the same position as with FIG. 3, it is to be noted that the flow direction is the same but the volume of liquid flow is reduced because the flow due to osmotic gradient has abated.

If it is desired to disinfect/rejuvenate the membranes of RO module 19 through descaling with acid, either before or after formaldehyde treatment, a suitable acid, such as hydrochloric acid (HCl) having a rejection range of approximately 97% to approximately 99% with respect to osmosis unit 19 can be appropriately utilized in a cleaned jug when flushed, following the same procedures of treatment and flushing as abovedescribed. The acid treatment can last for a suitable preselected period of time with a flushing period of approximately forty-five minutes or until monitor 24 indicates clearing of the system of disinfectant/rejuvenant fluid. Since the acid can hydrolize or soften the R.0. membrane, it then is advantageous to utilize a suitable alkali treating fluid such as sodium hydroxide (NaOH) in a jug 28, not only to reverse the acid effect on the membrane but to additionally defoul the membrane, the procedure again being the same with the exception that an alkali is generally osmotically inactive across RO unit 19 and the flow pattern would be similar to the flow pattern of FIGS. 2a, 3a and 4a. The alkali treatment can last for a suitable preselected period of time followed by a suitable final flushing period.

Figure 2A:
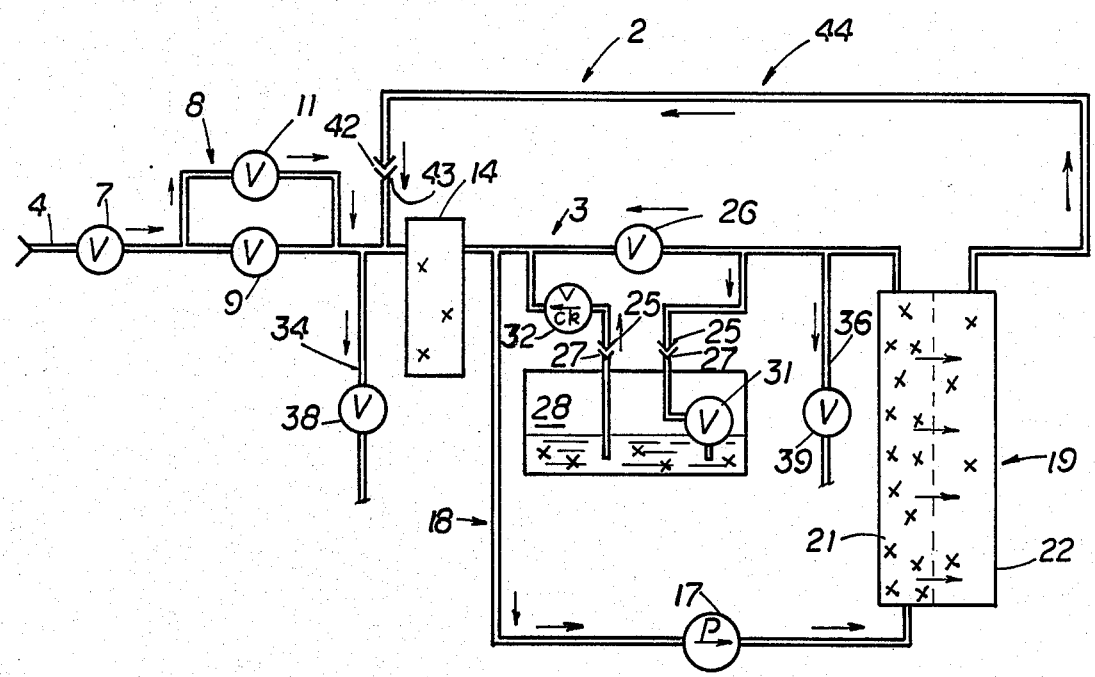
FIG. 2a is a view similar to that of FIG. 2, disclosing the direction of fluid flow when an osmotically inactive treating fluid is utilized.

Referring to FIGS. 2a and 5 with the valves in the same position as aforedescribed for FIG. 2, valves 7, 9 and 38 being closed and valves 11, 26, 31 and 32 being open and with an osmotically inactive fluid at a preselected low level in jug 28, flow is from jug 28, through valve 32, conduit loop 18, pump 17, the feed side of RO module 19, through recirculating valve 26 and through valve 31. Flow also is through the membrane of RO unit 19 since the fluid is osmotically inactive to the product side of the RO unit 19. Fluid then passes through global loop 44 to the inlet of prefilter 14 and returns through conduit loop 18 to pump 17. It is to be noted that movement of fluid to the product side of the membrane of RO unit 19 with an osmotically inactive fluid is a function of back pressure due to resistance to flow between the RO module 19 and jug 28. This resistance to flow can be established in a number of suitable ways and advantageously is established by a preselected sizing of float valve 31. It is to be understood that other flow resisting devices can be utilized, such as suitable diffusers, orifices or solenoid valves suitably positioned before or after valve 31. Advantageously the back pressure is in a range of approximately ten (10) to fifty (50) psi; this back pressure range does not prevent reverse osmotic flow when an osmotically active fluid is utilized in jug 28 as aforedescribed for FIG. 2 since osmotic pressures for an osmotic fluid are generally well above four hundred (400) psi—the back pressure being maintained in either an osmotically active or inactive fluid mode. Treatment with an osmotically active fluid lasts for a preselected period of time depending upon the nature of the fluid with equilibrium being reached by diffusion through the system and flow through global loop 44 being maintained.

Figure 3A:
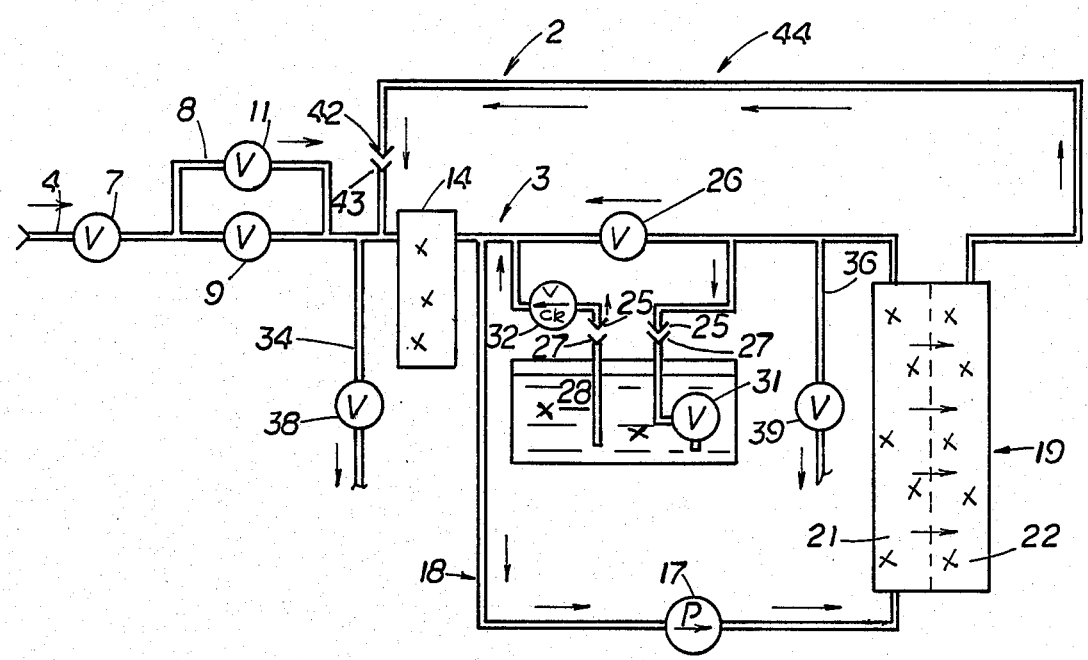
FIG. 3a is a view similar to that of FIG. 3, disclosing the direction of fluid flow when an osmotically inactive treating fluid is utilized.

Referring to FIGS. 3a and 5, at the commencement of flushing, with the valves in the same position as for FIG. 3 and with float valve 31 moving to an almost closed position to provide more back pressure causing valve 39 to open to drain and the volume of flow to drain to equal flow through open restricting valve 11, flushing continues until rejuvenant concentration reaches a satisfactory level. This flushing as abovedescribed lasts for approximately forty-five minutes. It is to be understood that instead of a sensing and control valve 31, it is possible to utilize a solenoid valve and float switch in those instances where larger volumes of fluid are involved and a float valve of suitable size is not readily available. It is further to be noted that flow to the product side of RO unit 19 during flushing with an osmotically inactive fluid is not affected by a forward osmotic gradient.

Figure 4A:
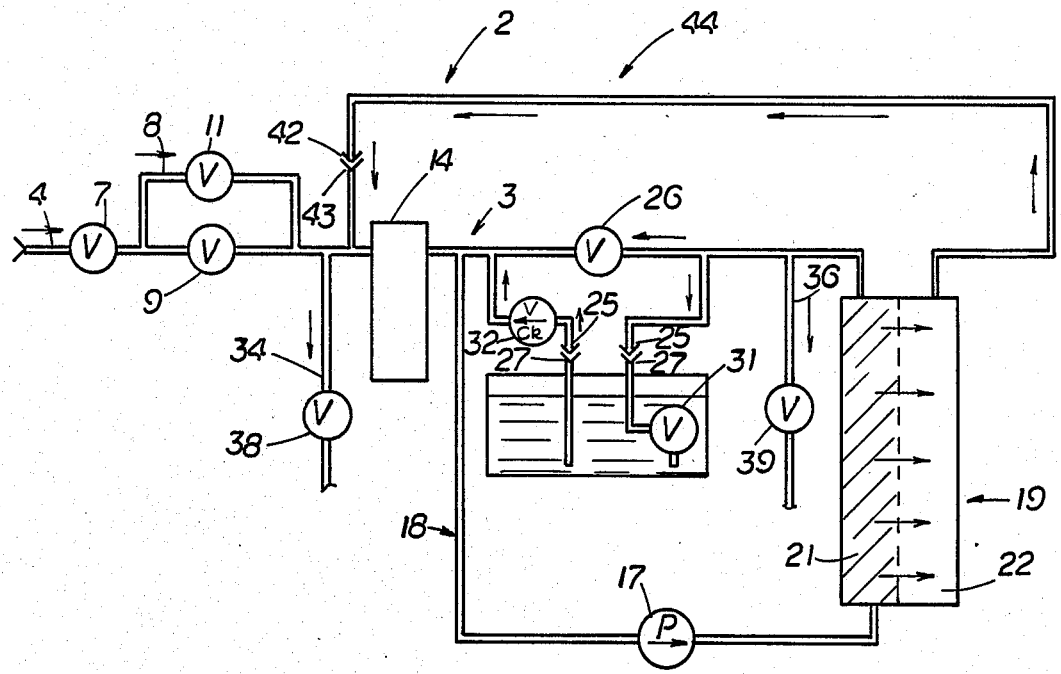
FIG. 4a is a view similar to that of FIG. 4, disclosing the direction of fluid flow when an osmotically inactive treating fluid is utilized; and, FIG. 5 is a symbolic legend disclosing fluid representations for feed water, product water, and low and high concentrations for osmotically active and osmotically inactive fluids.

Referring to FIGS. 4a and 5 which disclose the direction of flow for a non-osmotic fluid at the close of the flushing cycle and with the valves in the same position as for FIG. 4, the direction of fluid flow is the same as for FIG. 4 except that the osmotically inactive agent has been rinsed to an acceptable limit and feed water is shown as flowing through the system.

It is to be understood that the present invention is not limited to the specific chemicals aforedescribed. For example, osmotically inactive oxidants can be utilized in the disinfection/rejuvenation process.

After one or more of the treatment cycles abovedescribed, the mated quick connect fittings 42 and 43 are then disengaged and fluid purification resumed.

Thus, in accordance with the novel apparatus and a method of the present invention, it is now possible to purify and/or separate fluids in a straightforward, economical and efficient manner with a system treatment arrangement which is user-friendly in operation and maintenance with a minimum of toxic exposure and risk to both operator and user and, at the same time, achieve both an end fluid product which is highly purified and a purification arrangement which has been thoroughly disinfected/rejuvenated after each treatment for extended further use.

The invention claimed is:

1. A method of purifying fluid utilizing reverse osmosis comprising:
    passing fluid to be purified during a purifying cycle through an open ended feed zone, through a reverse osmosis zone to an open ended product zone and to an end user for a preselected time period;
    interrupting said purifying cycle after said preselected time period by closing said feed and product zones and recycling residual fluid in by-pass relation to said reverse osmosis zone from said product zone in direct, continuously circulating flow to said feed zone for a preselected time period during a treating cycle; and,
    introducing treating fluid from a treatment zone in direct, continuously circulating flow into the recycled fluid during said treating cycle to continuously disinfect/rejuvenate and flush said reverse osmosis zone throughout.

2. The method of claim 1, said treating fluid being osmotically active to allow residual fluid to osmotically pass from the product zone through said reverse osmosis zone to said feed zone during said treating cycle.

3. The method of claim 1, said treating fluid being an osmotically active bacteria disinfectant/rejuvenant to allow residual fluid to osmotically pass from said product zone through said reverse osmosis zone to said feed zone to uniformly disinfect the feed, reverse osmosis and product zone.

4. The method of claim 1, said treating fluid being an osmotically active formaldehyde solution having a rejection range of approximately 38% to approximately 50% with respect to the reverse osmosis zone to allow residual fluid to osmotically pass from said product zone through said reverse osmosis zone to said feed zone for a period of approximately one (1) to two (2) minutes to an equilibrium stage, said equilibrium stage lasting approximately one and one-half (1½) to two (2) hours.

5. The method of claim 1, said treating fluid being an osmotically active hydrochloric acid solution having a rejection range of approximately 97% to approximately 99% with respect to said reverse osmosis unit to allow residual fluid to osmotically pass from said product zone through said reverse osmosis zone to said feed zone for a preseected period to an equilibrium stage to be followed by a flushing stage of a preselected time period.

6. The method of claim 1, said treating fluid being an osmotically inactive alkali such as sodium hydroxide solution which would pass through the reverse osmosis zone from the feed zone to the product zone and be recycled back to the feed zone for a preselected time period to be followed by a flushing stage of a preselected time period.

7. The method of claim 1, said treatment fluid being a flushing fluid which is passed through the reverse osmosis zone from said treatment and feed zone to said product zone and recycled back to the treatment and feed zone for a preselected time period.

8. The method of claim 1, said treatment fluid being passed transverse the path of normal fluid flow through said reverse osmosis zone to be in shear-like, turbulent relation with respect to said normal flow path through said reverse osmosis zone.

9. The method of claim 1, said treatment fluid being a flushing fluid such as water which is passed through the reverse osmosis unit from the treatment and feed zone to the product zone and recycled back in direct, continuously circulating flow to the treatment and feed zone for a preselected time period, said flushing fluid passing through said zones at a controlled flow rate substantially equal to the passing of said flushing fluid to a drain zone.

10. The method of claim 1, said treating fluid being osmotically inactive with said feed zone including a subzone of preselected back pressure to enhance flow of said osmotically inactive fluid through said reverse osmosis zone.

11. The method of claim 1, said treating fluid being osmotically inactive with said feed zone including a subzone of preselected pressure between said reverse osmosis zone and said treatment zone to enhance flow of said osmotically inactive fluid through said reverse osmosis zone.

12. The method of claim 1, including sensing and controlling the introduction of said treating fluid to avoid system overflow and unintentional introduction of undesirable fluids during said treating cycle.

13. A method of purifying fluid utilizing reverse osmosis comprising:
    passing fluid to be purified during a purifying cycle for a time period of approximately three (3) to four (4) hours through an open ended feed zone, through a reverse osmosis zone in shearlike relation with the feedside thereof to an open ended product zone and to an end user;
    interrupting said purifying cycle at the end of said time period by closing said feed and product zones and recycling residual fluid in by-pass relation to said reverse osmosis zone from the product zone to the feed zone;
    introducing an osmotically active formaldehyde solution having a rejection range of approximately 38% to approximately 50% with respect to the reverse osmosis zone to allow residual fluid to osmotically pass from said product zone through said reverse osmosis zone to said feed zone for a period of approximately one to two minutes to an equilibrium stage, said equilibrium stage lasting for a suitable preselected period of time;
    passing a flushing fluid at a controlled rate equal to passing said fluid simultaneously to a drain zone through said reverse osmosis unit from said treatment and feed zone to said product zone and recycling same back to said feed and treatment zone for a suitable preselected period of time;
    repeating said treatment and flushing step with a solution of hydrochloric acid having a rejection range of approximately 97% to approximately 99% with said initial treating stage lasting for a preselected period of time to equilibrium state and said equilibrium state lasting for a suitable preselected period of time;
    passing an osmotically inactive sodium hydroxide solution in similar fashion as said flushing solution but without draining through said zones for a suitable preselected period of time; and,
    repeating said flushing cycle.

14. A fluid purification apparatus comprising:
    a primary flow conduit having spaced upstream fluid feed inlet means and downstream fluid product outlet means;
    a reverse osmosis means disposed in said primary flow circuit between said fluid feed inlet means and said fluid product outlet means to include a feed side and a product side;
    motive means communicating with said primary flow conduit to enhance fluid flow from said feed inlet means through said reverse osmosis means to said product outlet means;
    treatment means connectable into said primary conduit to selectively introduce separate treating fluids into said primary flow conduit to treat said reverse osmosis means; and
    a secondary flow global loop conduit connectable to extend parallel said primary flow conduit in by-pass relation to said reverse osmosis means to communicate in direct, continuously circulating flow between said product outlet means and said feed inlet means of said primary conduit and with said treatment means to continuously treat said reverse osmosis means throughout when a separate treating fluid is selectively introduced into said treatment means.

15. The fluid purification apparatus of claim 14, said secondary flow global loop conduit comprising part of the product side of said primary flow conduit reconnectable from the produce side in global loop fashion to the feed side of said primary flow conduit.

16. The fluid apparatus of claim 14, said treatment means including separate containers of treatment fluids.

17. The fluid purification apparatus of claim 14, said motive means being a pump positioned in communicative relation with said primary conduit between said feed inlet means of said primary conduit and said reverse osmosis means.

18. The fluid purification apparatus of claim 14, said treatment means being positioned in communicative relation with said primary conduit between said feed inlet means of said primary conduit and said reverse osmosis means.

19. The fluid purification apparatus of claim 14, said motive means and said treatment means being positioned in communicative relation with said primary flow conduit as part of a secondary closed loop conduit nested with said primary flow conduit.

20. The fluid purification apparatus of claim 14, said motive means and said treatment means being positioned in communicative relation with said primary flow conduit as part of a secondary closed loop conduit nested with said primary flow conduit and flow control means regulating relative flow in the primary flow conduit and the flow through said treatment means in said nested loop.

21. The fluid purification apparatus of claim 14, said motive means and said treatment means being positioned in communicative relation with said primary flow conduit as part of a secondary closed loop conduit nested with said primary flow conduit and flow control means including a flow restricting controller in said primary flow conduit and an inlet sensing and control and an outlet check valve arrangement in said treatment means to regulate the relative flow in the primary flow conduit and flow through said treatment means in said nested loop.

22. The fluid purification apparatus of claim 14, said motive means and said treatment means being positioned in communicative relation with said primary flow conduit as part of a secondary closed loop treating conduit nested in parallel relation with said primary flow conduit, said secondary closed loop conduit including a recirculation valve therein to control the amount of fluid circulation therethrough.

23. The fluid purification apparatus of claim 14, said motive means and said treatment means being positioned in communicative relation with said primary flow conduit between said feed inlet means and said feed side of said reverse osmosis means as part of a secondary closed loop treating conduit nested in parallel relation with said primary flow conduit.

24. The fluid purification apparatus of claim 14, said primary flow conduit having a prefilter disposed therein downstream of said feed inlet means with one end of said secondary global loop conduit being connectable to said primary flow conduit between said feed inlet means and said prefilter.

25. The fluid purification apparatus of claim 14, said primary flow conduit having quick connect fittings upstream and downstream said reverse osmosis means to cooperate with quick connect fittings at opposite ends of said secondary flow loop conduit to allow placing of said secondary global loop conduit in quick connected by-pass relation to said reverse osmosis means.

26. The fluid purification apparatus of claim 14, said treatment means communicating with said primary conduit through quick connect fittings.

27. The fluid purification apparatus of claim 14, said treatment means including a treating fluid container having treating fluid inlet and outlet conduits communicating with said primary flow conduit and container valve control means to regulate flow of fluid therethrough to said primary conduit.

28. The fluid purification apparatus of claim 14, said treatment means including a treating fluid container having treating fluid inlet and outlet conduits having quick connect fittings communicating with quick connect fittings in said primary flow conduit and valve control means cooperating with said container to regulate flow of fluid through said container to said primary conduit.

29. The fluid purification apparatus of claim 14, said primary conduit including a solvent feed control means disposed in said primary conduit to control the supply of fluid to be purified in accordance with the introduction of treatment fluid.

30. The fluid purification apparatus of claim 14, said primary conduit further including a fluid feed control means including a rinse control valve in said primary flow conduit downstream of said feed inlet means and a flow control restrictor in said primary conduit in parallel with said rinse control valve to control the supply of fluid therethrough in accordance with the introduction of treatment fluid.

31. The fluid purification apparatus of claim 14, said primary conduit including a flow restrictor and said treatment means including a vented treating fluid container having treating fluid inlet and outlet conduits communicating with said primary flow conduit and level sensing and check valve members cooperating with said container inlet and outlet to regulate flow of fluid through said container to said primary conduit.

32. The fluid purification apparatus of claim 14, said primary circuit including fluid drain control means and a fluid condition monitor means operative to open said drain control means when fluid conditions in said primary conduit reach a preselected condition.

33. The fluid purification apparatus of claim 14, said primary conduit including fluid drain control means and pressure limit valve control means operative to open said drain control means when fluid pressures in said primary conduit reach a preselected pressure level.

34. The fluid purification apparatus of claim 14, said primary circuit including fluid drain control means and pressure limit control means on both feed and product sides of said reverse osmosis means to selectively open each of said drain control means when preselected fluid pressure levels have been reached in the primary circuit on each side of said reverse osmosis means.

35. The fluid purification apparatus of claim 14, said primary circuit including fluid drain control means and a fluid current conductivity/resistivity monitor means operative to open said drain control means when fluid current conductivity/resistivity conditions in said primary circuit reach a preselected current level.

36. The fluid purification apparatus of claim 14, said primary conduit including fluid drain control means, and a fluid current conductivity/resistivity monitor means operative to open said drain control means when fluid current conductivity/resistivity conditions in said primary conduit reach a preselected current level; and means to render said current conductivity/resistivity monitor means inoperative with respect to such drain control means when said secondary flow loop conduit is connected to said primary conduit in by-pass global loop relation to said reverse osmosis means.

37. The fluid purification apparatus of claim 14, said primary flow conduit including pressure restrictive means on said feed side of said reverse osmosis means to permit use of osmotically inactive fluids in said purification apparatus.

38. The fluid purification apparatus of claim 14, said primary flow conduit including pressure restrictive means between said feed side of said reverse osmosis means and said means connectable to said primary conduit to selectively introduce separate treating fluids.

39. A fluid purification apparatus comprising:
a primary flow conduit having spaced upstream fluid feed inlet means and downstream fluid product outlet means;
a reverse osmosis means disposed in said primary flow conduit between said fluid feed inlet means and said fluid product outlet means to include a feed side and a product side;
said primary flow conduit successively including downstream of said feed inlet means and before said reverse osmosis means, a carbon treating tank, a rinse control valve having a flow control restrictor parallel thereto, a prefilter, and a recirculating valve;
said primary flow conduit further including solvent drain control means and pressure limit control means on both feed and product sides of said reverse osmosis means to selectively open each of said drain control means when preselected fluid pressure levels have been reached in the primary circuit on each side of said reverse osmosis means and also including a conductivity/resistivity monitor means on said product side of said reverse osmosis means to open said drain control means when fluid current conductivity/resistivity conditions in said primary circuit reach a preselected level;

pump means positioned in communicative relation with said primary conduit as part of a secondary nested closed loop treating conduit nested in parallel relation with said primary conduit before said recirculating valve and said feed side of said reverse osmosis means;

treatment means communicating with said primary conduit through quick connect fittings on opposite sides of said recirculating valve, said treatment means including a vented treating fluid container having inlet and outlet conduits communicating with said primary flow conduit through said quick connect fittings and further including an inlet sensing and control valve sized to provide a preselected flow restriction and an outlet check valve in said container to regulate flow of fluid through said container to said primary conduit and through said drain control means in accordance with fluid level in said container; and, a secondary flow global loop conduit having quick connect fittings, at opposed ends thereof connectable to primary conduit fittings to extend parallel said primary flow conduit in by-pass relation to said reverse osmosis means to communicate directly between said product outlet means and said feed inlet means of said primary conduit and with said treatment means to flush said reverse osmosis means when a separate chemical treating fluid is selectively introduced into said treatment means, said primary flow conduit having quick connect fittings upstream said feed side of said reverse osmosis means and said prefilter and downstream said conductivity/resistivity monitor means on said product side of said reverse osmosis means to cooperate with quick connect fittings of said secondary flow loop conduit to allow placing of said secondary global loop conduit in by-pass relation to said reverse osmosis means, said quick connect fittings in said global loop including means to render said current conductivity/resistivity detection means inoperative with respect to drain when said secondary flow loop conduit is connected to said primary conduit in by-pass relation to said reverse osmosis means.

* * * * *

UNITED STATES PATENT AND TRADEMARK OFFICE
CERTIFICATE OF CORRECTION

PATENT NO. : 4,784,771
DATED : 11-15-88
INVENTOR(S) : Ronald L. Wathen and Steven L. Miller It is certified that error appears in the above—identified patent and that said Letters Patent is hereby corrected as shown below:

Column 7, line 30, correct "is" to ---are---;

Column 7, line 35, correct "its" to ---their---;

Column 12, line 29 (Claim 15, line 4) correct "produce" to ---product---.

Signed and Sealed this

Eleventh Day of April, 1989

Attest:

DONALD J. QUIGG

Attesting Officer

Commissioner of Patents and Trademarks